United States Patent [19]
Ikonen et al.

[11] Patent Number: 6,083,462
[45] Date of Patent: Jul. 4, 2000

[54] SPECIMEN IDENTIFIER

[76] Inventors: Pasi Ikonen, Kalevalankatu 13 H 6, Fin-70500 Kuopio; Reijo Tuononen, Kettulanlahdentie 73, Fin-70400 Kuopio, both of Finland

[21] Appl. No.: 09/081,939

[22] Filed: May 21, 1998

Related U.S. Application Data

[63] Continuation of application No. PCT/FI96/00630, Nov. 21, 1996.

[30] Foreign Application Priority Data

Nov. 22, 1995 [FI] Finland ..................................... 955611

[51] Int. Cl.[7] .............................. G06F 17/00; B01L 9/06
[52] U.S. Cl. ......................... 422/104; 422/102; 235/375; 235/385; 235/441; 235/486; 235/487
[58] Field of Search .................................... 422/102, 104, 422/99, 67; 235/375, 385, 441, 486, 487, 439, 451, 492

[56] References Cited

U.S. PATENT DOCUMENTS

| | | | |
|---|---|---|---|
| 3,612,321 | 10/1971 | Larson | 422/102 |
| 3,680,967 | 8/1972 | Englehardt | 422/102 |
| 3,788,450 | 1/1974 | Tschunt et al. | 198/131 |
| 3,818,188 | 6/1974 | Hertel et al. | 238/483 |
| 4,944,924 | 7/1990 | Mawhirt et al. | 422/104 |
| 5,397,542 | 3/1995 | Nelms et al. | 422/104 |
| 5,456,887 | 10/1995 | Calvo et al. | 422/104 |
| 5,777,303 | 7/1998 | Berney | 422/104 |

FOREIGN PATENT DOCUMENTS

| | | |
|---|---|---|
| 931617 | 10/1994 | Finland . |
| 43 06 563 | 9/1994 | Germany . |

*Primary Examiner*—Gary K. Graham
*Attorney, Agent, or Firm*—Pillsbury Madison & Sutro LLP

[57] ABSTRACT

The subject of this invention is a specimen identifier, which consists of a base section (1), which allows the specimen identifier to be placed on a surface, an identifier memory unit (2) for identifying the specimen, which fits conveniently into the base section, and a mounting section (3) for mounting the test tube (4) in the specimen identifier. According to the invention, the specimen identifier includes a middle section (5) between the base section (1) and the mounting section (3), and mounting grips (3) forming the mounting section positioned a short distance from the base section (1) which expand to the sides, are curve-shaped and manufactured from a flexible material, and whose arms are a distance apart from each other and between which the test tube can be mounted.

4 Claims, 3 Drawing Sheets

SPECIMEN IDENTIFIER

This is a continuation of: International Appln. No. PCT/FI96/00630 filed Nov. 21, 1996 which designated the U.S.

The subject of this invention is a specimen identifier, which consists of a base section, which allows the specimen identifier to be placed on a flat surface, an identifier memory unit for identifying the specimen, which fits conveniently into the base section, and a mounting section for mounting the test tube in the specimen identifier.

BACKGROUND OF THE INVENTION

At present, it is general practice to place the test tube, or an equivalent vessel containing the specimen, into specific specimen identifiers and then to transfer the specimen identifiers from one appliance to another during the various handling stages of the specimen. Data can then be fed into the memory of the specimen identifier for identification purposes. Typical data would be the personal details or identifier of the specimen owner for identification purposes, the tests performed, or to be performed, on the specimen, etc. There are disadvantages associated with present specimen identifiers. Visibility of the specimen is an important factor, but with present equipment, it is not possible to view the specimen sufficiently clearly since the specimen holder covers the test tube. With present appliances or holders the test tube is mounted by pushing it down from above until the bottom of the test tube touches the base section. Inserting and removing test tubes in this manner is, however, difficult. It is also a problem if the specimen identifier cannot stand up to the operations required by the test programme.

SUMMARY OF THE INVENTION

The purpose of this invention is to introduce a specimen identifier which eliminates the drawbacks associated with the present specimen identifiers. In particular, the purpose of the invention is to introduce a specimen identifier in which the specimen is clearly visible and in which the specimen identifier, test tube and specimen can be easily handled. In addition, the purpose of the invention is to introduce an enduring specimen identifier in which the test tube, or equivalent, is easily mounted and from which it is easily removed.

The purpose of the invention is achieved with a specimen identifier which possesses the characteristics presented in the appended patent claims.

According to the invention, the specimen identifier includes a middle section between the base section and the mounting section, and mounting grips forming the mounting section positioned a short distance from the base section which expand to the sides, are curve-shaped and manufactured from a flexible material, and whose arms are a distance-apart from each other and between which the test tube can be mounted. These mounting grips clamp the test tube, or equivalent vessel, tightly and the tube remains well in position, also supported from below by the base section of the specimen identifier.

With this invention, the following advantages are also achieved; the specimen is clearly visible in the specimen identifier throughout the whole of the middle section and between the mounting grips. The specimen identifier can be used over and over again. The specimen identifier accompanies the specimen from the taking of the specimen through to its analysis. The specimen tube remains reliably in the specimen identifier, neither does the specimen identifier damage the specimen tube. The specimen identifier can easily be cleaned and withstands laboratory conditions such as in an autoclave or deep-freezing. The specimen identifier is manufactured economically from a suitable material by a process such as injection molding.

The middle section of the invention is advantageously curve-shaped and the length of the curve formed by it is essentially smaller that the curve formed by the mounting section. In this way, the specimen tube can also be placed against the middle section but it does not prevent the mounting and removal of the specimen tube.

The specimen tube is mounted in the specimen identifier by placing the bottom of the tube into the specimen identifier and by pressing the tube between the mounting grips with a levering movement. The bottom of the tube can be placed against the base section because the middle section does not prevent this action. The mounting grips are free to move in opposite directions because they are some distance from the base section neither does the middle section inhibit their movement. Removal is carried out by continuing the levering movement in the same direction. The mounting and removal of the specimen are simply and easily carried out.

In the advantageous additional arrangement of the invention the external diameter of the mounting section is smaller than the external diameter of the base section. When the specimen tube is placed in the mounting section, the mounting section spreads outwards to a certain extent due to the flexibility of the material. When the specimen tube is in position, the external diameter of the mounting section is approximately as wide, or slightly wider than, the external diameter of the base section. The external diameter of the mounting section is such that it permits the placing of the specimen identifier in standard-size stands, appliances or equivalent.

BRIEF DESCRIPTION OF THE DRAWINGS

In the following, the invention is defined in more detail with reference to the attached illustrations, in which.

DETAILED DESCRIPTION OF THE DRAWINGS

Figure 1:
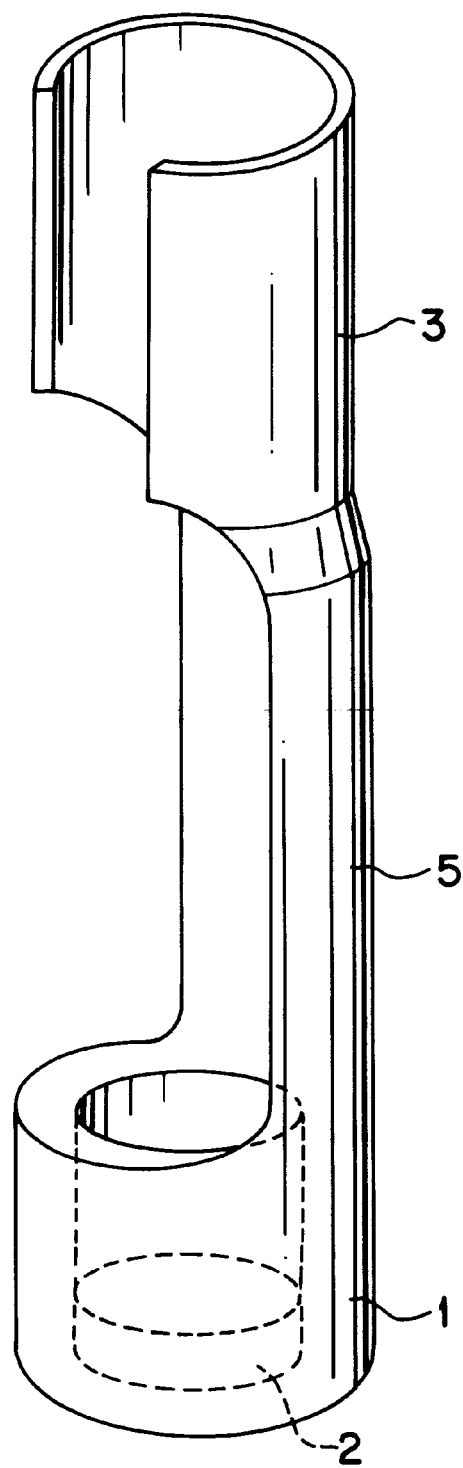
FIG. 1 shows an arrangement of the specimen identifier, seen from the side.

In the arrangements shown in the figures, the specimen identifier consists of a base section 1, a middle section 5, and a mounting section 3. The base section is hollow and an identifier memory unit 2 is placed in this space. The hollow space in the base is closed with a base plate, such that the identifier memory unit remains tightly within the enclosed space. The center of gravity of the specimen identifier is close to the base section and the base section is shaped conveniently flat and, in any case, such that the specimen identifier remains standing also when the specimen tube 4 is mounted into it. The upper surface of the base section is shaped with a cup-shaped indentation.

The identifier memory unit 2, situated in the base section, contains a memory component and transmitter/receiver. The identifier memory unit is connected permanently to the specimen identifier at the assembly stage. The identifier memory unit contains the required data concerning the patient, the specimen and its handling. The identifier memory unit is such that it can be re-used and new data can again be entered. A standard identifier memory unit, suitable for the purpose, is generally used as the identifier memory unit.

The mounting section has curved, expanding, mounting grips 3 which are made from a suitable flexible material. The grips are a small distance apart from each other. The middle section 5 is between the base section 2 and the mounting section 3, such that the mounting section is at a distance from the base section. The middle section 5 is curved-shaped and the length of the curve formed is essentially smaller than the curve formed by the mounting section.

The external diameter of the mounting section is smaller than the external diameter of the base section. This is achieved by changing the diameter of the casing between the upper and middle section such that there is a beveling at this point. In this way there are no sharp edges and the surface tapers evenly.

The specimen identifier is open from the side such that the specimen is visible throughout its length. The upper section of the specimen identifier around the tube has a partially round, friction and gripping surface.

Figure 3:
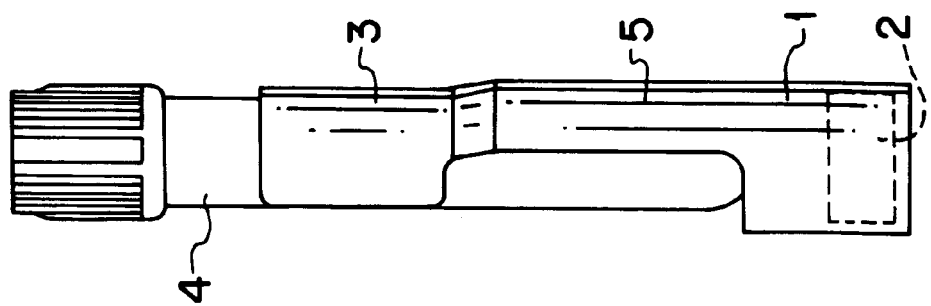
FIG. 3 shows the specimen tube mounted in the specimen identifier.
Figure 2:
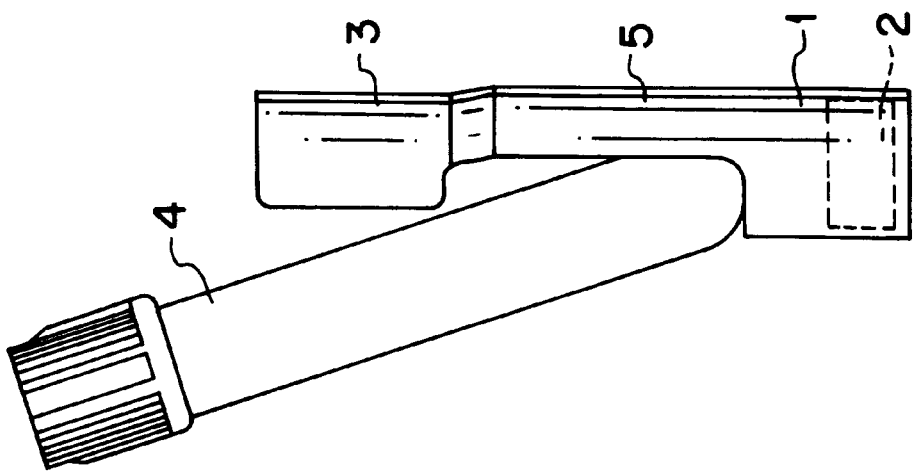
FIG. 2 shows the mounting of the specimen tube in the specimen identifier, seen from the side.

The specimen tube is mounted in the specimen identifier as shown in FIGS. 2–3 such that the bottom of the specimen tube is placed against the base of the specimen identifier and by twisting and levering the specimen tube towards the mounting section, where the mounting grips of the mounting section spread and the specimen tube can be pushed between them. Once the specimen tube is attached, the mounting grips press the specimen tube tightly in place.

Figure 4:
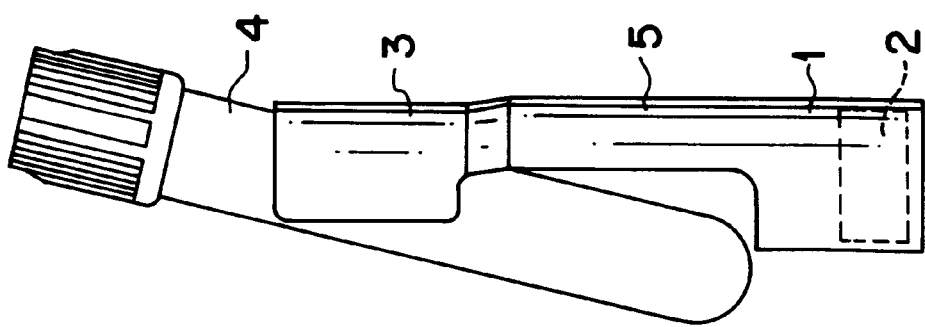
FIG. 4 shows the removal of the specimen tube, seen from the side.

Removal is carried out according to FIG. 4 by continuing the levering movement in the same direction as in mounting. in this way the bottom of the test tube becomes detached first and by continuing to twist, the top part is also separated from between the mounting grips.

Figure 5:
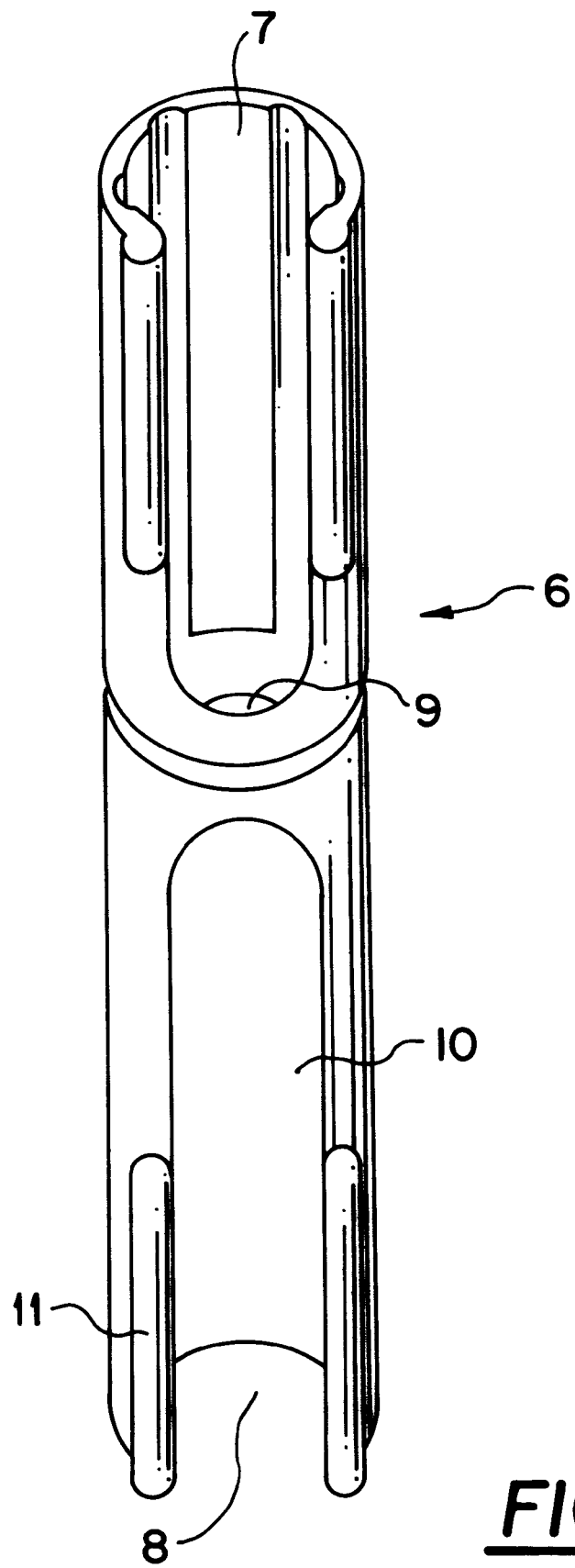
FIG. 5 shows an adapter for use with a specimen tube, seen from the side.

The specimen identifier also includes an adapter 6, as shown in FIG. 5 which is intended for mounting smaller test tubes, such as micro tubes, to the specimen identifier. The adapter contains two recessions 7, 8, intended for different tube sizes having different size diameters. The recessions are one on top of the other and between them there is a middle section 9. Grooves 10 have been made around one rim of the recession in a vertical direction, through which the specimen tube fitted in them can be seen. The grooves 10 of the adapter have bulging edges 11 with which the adapter can be mounted in the correct position in the specimen identifier such that the grooves are visible.

The invention is not limited to the advantageous arrangements shown but can vary within the framework of the invention concept formed by the patent claims.

We claim:

1. The specimen identifier comprising:
   a base section by which the specimen identifier can be placed on a flat surface,
   an identifier memory unit placed in the base section, for identifying the specimen, and
   a mounting section for mounting a test tube to the specimen identifier, wherein
      the specimen identifier contains a middle section between the base section and the mounting section,
      the mounting section includes mounting grips a distance from the base section which expand sideways, are curve-shaped, made from a flexible material and having arms which are a distance from each other and between which the test tube can be mounted, and
      the middle section is curve-shaped and the length of the curve formed is smaller than the curve formed by the mounting section.

2. A specimen identifier according to the claim 1, characterised in that the external diameter of the mounting section is smaller than the external diameter of the base section.

3. A specimen identifier according to the claim 1, wherein the external diameter of the mounting section is smaller than the external diameter of the base section.

4. A specimen identifier according to the claim 1, wherein the upper surface of the base section has a cup-shaped formation for a bottom of the test tube.

* * * * *

UNITED STATES PATENT AND TRADEMARK OFFICE
CERTIFICATE OF CORRECTION

PATENT NO.   : 6,083,462
DATED        : July 4, 2000
INVENTOR(S)  : Ikonen et al.

It is certified that error appears in the above-identified patent and that said Letters Patent is hereby corrected as shown below:

<u>Title page,</u>
Please add: -- [73]  Assignee:  Clids Oy, Kuopio, Finland --

Signed and Sealed this

Eighth Day of April, 2003

JAMES E. ROGAN
*Director of the United States Patent and Trademark Office*